US012390545B2

(12) United States Patent
Smith

(10) Patent No.: US 12,390,545 B2
(45) Date of Patent: Aug. 19, 2025

(54) OPEN-CELL FOAM BASED PATHOGEN REMEDIATION

(71) Applicant: Scott C. Smith, Osterville, MA (US)

(72) Inventor: Scott C. Smith, Osterville, MA (US)

( * ) Notice: Subject to any disclaimer, the term of this patent is extended or adjusted under 35 U.S.C. 154(b) by 900 days.

(21) Appl. No.: 17/467,256

(22) Filed: Sep. 5, 2021

(65) Prior Publication Data

US 2022/0088247 A1 Mar. 24, 2022

Related U.S. Application Data

(63) Continuation-in-part of application No. 15/987,664, filed on May 23, 2018, now Pat. No. 11,112,397, which is a continuation-in-part of application No. 15/454,626, filed on Mar. 9, 2017, now abandoned.

(51) Int. Cl.

| | |
|---|---|
| ***A61L 2/18*** | (2006.01) |
| ***A61L 9/14*** | (2006.01) |
| ***C02F 1/50*** | (2023.01) |
| ***C12Q 1/02*** | (2006.01) |
| ***C12Q 1/04*** | (2006.01) |
| ***G01N 1/12*** | (2006.01) |
| ***G01N 1/16*** | (2006.01) |
| ***G01N 1/22*** | (2006.01) |
| ***G01N 1/28*** | (2006.01) |
| ***G01N 33/18*** | (2006.01) |
| ***G01N 33/497*** | (2006.01) |
| *G01N 1/10* | (2006.01) |

(52) U.S. Cl.

CPC ................. *A61L 2/18* (2013.01); *A61L 9/145* (2013.01); *C02F 1/50* (2013.01); *C12Q 1/02* (2013.01); *C12Q 1/04* (2013.01); *G01N 1/12* (2013.01); *G01N 1/16* (2013.01); *G01N 1/2214* (2013.01); *G01N 1/2273* (2013.01); *G01N 1/2813* (2013.01); *G01N 33/1826* (2013.01); *G01N 33/497* (2013.01); *A61L 2209/21* (2013.01); *A61L 2209/22* (2013.01); *C02F 2303/04* (2013.01); *G01N 2001/1056* (2013.01); *G01N 2001/2826* (2013.01); *G01N 33/184* (2024.05); *G01N 2333/37* (2013.01)

(58) Field of Classification Search

CPC .......... G01N 1/12; G01N 1/16; G01N 1/2214; G01N 1/2273; G01N 1/2813; G01N 33/1826; G01N 33/497; C12Q 1/02; C12Q 1/04; C02F 1/50; A61L 2/18; A61L 9/145

See application file for complete search history.

(56) References Cited

U.S. PATENT DOCUMENTS

| | | | | |
|---|---|---|---|---|
| 5,792,712 A * | 8/1998 | Hori | A01N 25/34 | 15/104.93 |
| 6,331,514 B1 * | 12/2001 | Wurzburger | C11D 7/20 | 134/41 |
| 2013/0240451 A1 * | 9/2013 | Curtis, Jr. | C08J 9/0061 | 521/149 |
| 2017/0304815 A1 * | 10/2017 | Vachon | C08L 57/06 | |

* cited by examiner

*Primary Examiner* — Lyle Alexander
*Assistant Examiner* — Dwan A Gerido
(74) *Attorney, Agent, or Firm* — Brian M. Dingman; Prince Lobel Tye LLP

(57) ABSTRACT

An open-cell foam structure that is impregnated with a disinfectant and used to remove pathogens from air, water, and surfaces, and kill the pathogens.

12 Claims, 1 Drawing Sheet

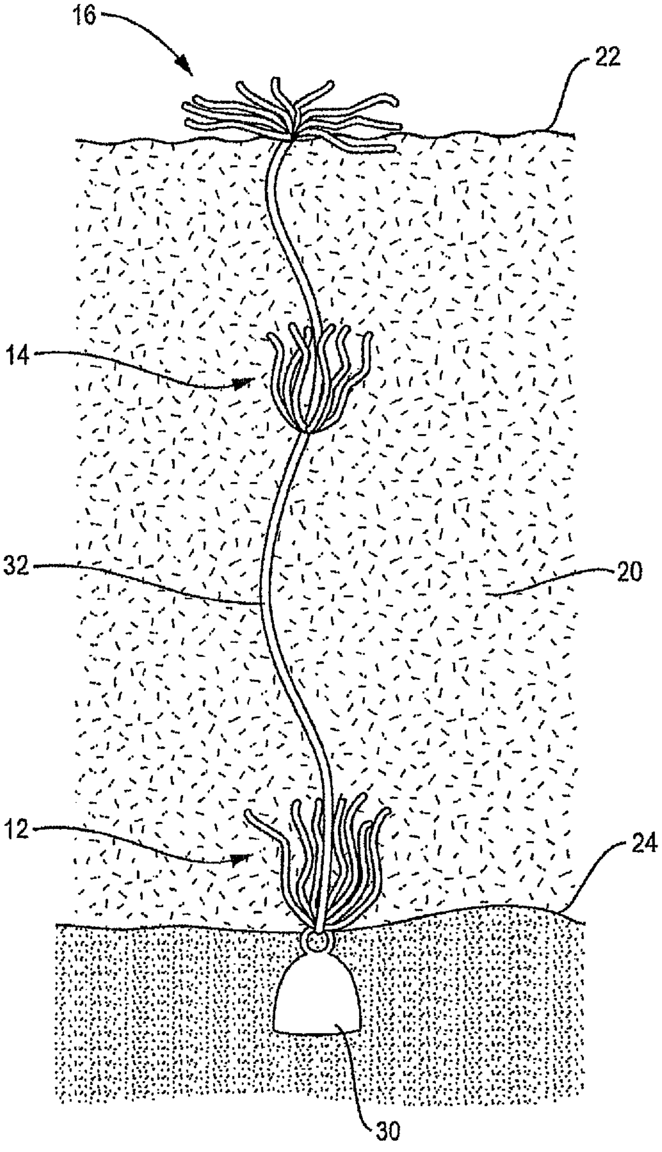
16
22
14
32
20
12
24
30

OPEN-CELL FOAM BASED PATHOGEN REMEDIATION

CROSS-REFERENCE TO RELATED APPLICATIONS

This application claims priority of Provisional Patent Application 62/510,091, filed on May 23, 2017, the entire disclosure of which is incorporated herein by reference. This application is also a continuation in part of and claims priority of both application Ser. No. 15/987,664, filed on May 23, 2018, which is itself a continuation in part and claims priority of application Ser. No. 15/454,626, filed Mar. 9, 2017. The entire disclosures of each of these prior Applications are incorporated herein by reference.

BACKGROUND

Microbiological or biological contamination includes but is not limited to pathogens, which include bacteria, fungi, mold, protozoa, virus, or other microorganism that can cause disease (collectively referred to as pathogens) and/or their associated toxins and byproducts. Such biological contamination is never in equilibrium or evenly distributed in water or air or on surfaces, let alone water or air that is constantly flowing with many other variables to consider. Furthermore, to this day, there is not much known about biofilms and their respective formation and variability with changing conditions in aging infrastructures and variability in water treatment methods. Instantaneous/grab sampling reflects what is in the water or air for a split second, assumes the water or air being tested is in equilibrium, and does not take into consideration conditions like the mixture of fresh water to bacteria of concern when the grab sample is taken.

The significance of bacteria, viruses and other pathogens of concern in our water and air and on surfaces are of increasing interest due to their known and unknown effects on human health, antibiotic resistance, as well as the health of animals and plants, and effects on the ecosystem. Animals and humans that are exposed to contaminated water or air can be exposed to pathogens.

Traditional sampling by collecting and analyzing a split second "grab sample" has several limitations. Among those limitations is the inability to detect transient biological contaminants or pathogens that are discharging (including but not limited to releasing from biofilms) sporadically and diffusing through the water, water column, water stream, or body of water on an irregular basis, and the limited sample size that may contain only undetectable amounts of contaminants that are present at low concentration. Also, grab samples, by their nature, are instantaneous and testing results only represent the volume of water that is in the sample bottle/container. As a fish does not swim in the water for a split second and neither does a child, it is desired to have a sampling process that involves actual exposure over time and/or exposure to larger volumes of water beyond just the volume of the bottle/container (with a small volume of water from 250 ml to 1 liter) with corresponding identification of biological contaminants over time in the same way that life forms are exposed to contaminants over time throughout more than just a limited volume of water. In essence, this subject disclosure is based on biomimicry.

To better understand this disclosure, it is helpful to understand the background of biological contamination and pathogens more generally, and various methods that have been used to monitor biological contamination and pathogens more generally. Heterotrophs are broadly defined as microorganisms that require organic carbon for growth. They include bacteria, yeasts and molds. Also, this includes bacteria that utilize iron, copper, and phosphorus-related compounds as nutrients or food sources. A variety of simple culture-based tests that are intended to recover a wide range of microorganisms from water are collectively referred to as "heterotrophic plate count" or "HPC test" and "aerobic plate count" or "APC test" procedures. For purposes of this disclosure HPC and APC tests are used synonomously.

However, the terms "heterotroph" and "HPC" are not synonymous. There is no universal "HPC measurement." Although standardized methods have been formalized, HPC test methods involve a wide variety of test conditions that lead to a wide range of quantitative and qualitative results. Temperatures employed range from around 20° C. to 40° C., incubation times from a few hours to seven days or a few weeks, and nutrient conditions from low to high. The test itself does not specify the organisms that are detected. Only a small proportion of the metabolically active microorganisms present in a water sample may grow and be detected under any given set of HPC test conditions, and the population recovered will differ significantly according to the method used. The actual organisms recovered in HPC testing can also vary widely between locations, between seasons and between consecutive samples at a single location.

Microorganisms recovered through HPC tests generally include those that are part of the natural (typically non-hazardous) microbiota of water; in some instances, they may also include organisms derived from diverse pollutant sources.

Microorganisms will normally grow in water and on surfaces in contact with water as biofilms. Growth following drinking-water treatment is normally referred to as "regrowth." Growth is typically reflected in higher HPC values measured in water samples. Elevated HPC levels occur especially in stagnant parts of piped distribution systems, in domestic plumbing, in bottled water and in plumbed-in devices, such as softeners, carbon filters and vending machines. The principal determinants of regrowth are temperature, availability of nutrients and lack of residual disinfectant. Nutrients may be derived from the water body and/or materials in contact with water.

There is no evidence, either from epidemiological studies or from correlation with occurrence of waterborne pathogens, that HPC values alone directly relate to health risk. They are therefore unsuitable for public health target setting or as sole justification for issuing "boil water" advisories. Abrupt increases in HPC levels might sometimes concurrently be associated with faecal contamination; tests for *E. coli* or other faecal-specific indicators and other information are essential for determining whether a health risk exists. There is an unmet need for cost effective and efficient identification of biological contamination in conjunction with HPC values; this is one of the benefits of the subject disclosure.

In piped distribution systems, HPC measurements are assumed to respond primarily to (and therefore provide a general indication of) distribution system conditions. These arise from stagnation, loss of residual disinfectant, high levels of assimilable organic carbon in the water, higher water temperature, and availability of particular nutrients. In systems treated by chloramination or that contain ammonia in source waters, measurement of a variety of parameters, including HPC, but especially including nitrate and nitrite (which are regulated for health protection), can sometimes indicate the possible onset of nitrification. This illustrates the importance of monitoring for exposure over time with the subject disclosure.

Some epidemiological studies have been conducted into the relationship between HPC exposures from drinking water and human health effects. Other studies relevant to this issue include case studies, especially in clinical situations, and compromised animal challenge studies using heterotrophic bacteria obtained from drinking-water distribution systems. The available body of evidence supports the conclusion that, in the absence of faecal contamination, there is no direct relationship between HPC values in ingested water and human health effects in the population at large. This conclusion is also supported indirectly by evidence from exposures to HPC in foodstuffs, where there is no evidence for a health effects link in the absence of pathogen contamination.

There are opportunistic pathogens that may regrow in water but that are not detected in HPC measurements, including strains of *Legionella* and non-tuberculous mycobacteria. The public health significance of inhalation exposure to some legionellae has been demonstrated. Again, since the HPC or APC is one general indicator, this is another example of why the subject disclosure is important with its ability to identify pathogenic bacteria including exposure over time.

The growth of bacteria in water distribution systems and water treatment devices has been recognized for many years. Such growth is affected by many different factors, including the types of bacteria present in water released from a water treatment plant, the temperature, disinfectant concentration, the presence of sediment in the pipe work, the types and amount of nutrients present, and the rate of flow of the water. Many of these factors cannot be controlled, and thus microbial regrowth will continue to be investigated. The organisms involved in microbial regrowth are those that have been released from the water treatment plant or that have been introduced into the distribution system at some point downstream of the water treatment plant. If it is assumed that the water treatment plant is performing adequately, then the numbers of bacterial pathogens released into the water distribution system will be low, and those that are present are likely to be killed during transport in systems where residual disinfectant is present. However, a break in the integrity of the distribution system (e.g., burst water main) can lead to the ingress of contaminated water. Such water may contain organisms that are potentially pathogenic for humans.

Many bacteria that enter the water distribution system are unable to survive or indeed colonize the distribution system, but many bacteria, including indicator bacteria such as *Enterobacter, Citrobacter* and *Klebsiella*, as well as potentially opportunistic pathogens such as *Aeromonas, Pseudomonas, Flavobacterium* and *Acinetobacter*, are often found in colonized water distribution systems.

Biofilms represent a specific form of bacterial colonization of water distribution systems. These specific forms determine the biostability of the microbial communities, their persistence and the release of planktonic cell microorganisms into the running water. The biofilms interact with waterborne pathogens and affect their persistence. The persistence of these pathogens is considerably increased if they form a new biofilm or colonize an existing one. The biofilms thus represent bioreactors within water distribution systems, in which the resistance of the microorganisms to disinfection is significantly increased. The potential for biofilm formation and growth is particularly high in narrow-gauge household plumbing. The colony count is directly correlated with the water volume that flows through these end-of-line systems.

SUMMARY

It is desirable to have an accurate and cost efficient method to remediate, collect and analyze water and air samples and surfaces for biological contamination for large volumes of water and/or exposure over time. It is also desirable to remediate pathogens in the air, in water, and on surfaces, using chemical-based and/or hydronium-based disinfectants.

This disclosure relates to remediating, detecting, removing, and killing bacteria, viruses, and other biological contaminants and pathogens from water and/or air and/or surfaces. Open-cell foam matrix cumulative/exposure testing not only identifies bacteria of concern and corresponding colony formation units ("CFU") but what the actual exposure is in the water or air or surfaces over time. The disclosure also results in removal/filtration of bacteria, mold, viruses and other organisms and pathogens from the water or air or surfaces. The foam that is used in the open-cell foam structures can be impregnated with one or more biocides and/or disinfectants, or another chemical or substance that can kill or neutralize pathogens which include bacteria, viruses, or other microbiological or biological organisms and other biological contaminants.

One subject of this disclosure is an open-cell foam. The open-cell foam can be made from various polymers. In one non-limiting example, the foam is produced from a copolymer of ethylene and alkyl acrylate. The foam can comprise an elastomeric polyolefin. Examples of elastomeric polyolefins include but are not limited to ethylene methyl acrylate (EMA) and a single site initiated polyolefin elastomer (e.g. Dow or DuPont Dow Engage 8452) The open-cell foam is composed of a polyolefin elastomer which includes but is not limited relatively amorphous elastomers and/or includes blends of other polymers. The open-cell structure of the various foams behaves as the alveoli of the human lungs in that it maximizes surface area which maximizes the efficacy of the open-celled foam's ability to attract biological and related contamination at the molecular level. The foam is hydrophobic and so repels water. Because the foam is hydrophobic it does not promote bacterial or pathogen growth which makes it naturally antimicrobial without additional additives.

The open-celled foam structure provides high surface area due to the interconnected structure of the individual cells. The oleophilic nature of the constituent polymer(s) prevents the absorption of water and promotes absorption and adsorption of oils and other organic substances such as pathogens and viruses.

The structure that includes or is made of open-cell foam can be fabricated from a very specific formulation for an open-cell foam. Specifically, this foam is produced from 80-100% ethylene acrylate copolymer. Blends of LDPE (low density polyethylene) can be used also. One embodiment/formulation of this open-cell foam is described in U.S. Pat. No. 8,853,289, the disclosure of which is incorporated herein by reference. Another embodiment/formulation of this open-cell foam is described in patent application US2013/0240451 A1, the disclosure of which is incorporated herein by reference. While 80-100% EMA (ethylene methyl acrylate) is one formulation of the open-cell foam that is substantially non-polar, what is contemplated herein includes any open-cell foam produced from one or more polymers including but not limited to EVA (ethyl vinyl acetate), EPDM (ethylene propylene diene monomer), elastomers, LDPE, polypropylene, neoprene, styrene butadiene rubber, ionic co-polymers, natural rubber, single site initiated or metallocene polyolefins and equivalents. The preferred foam density is in the range of from about 1.0 pcf (pounds per cubic foot) to about 50.0 pcf, but the foam can be any density less than the specific gravity of water (62.3 pcf at 70° F.). The open-cell foam can be extruded or produced in a bun/batch process. The open-cell foam can be crosslinked or non-crosslinked. Also, the open-cell foam can utilize either physical blowing agents or chemical blowing agents. Furthermore, a bio-degradable initiator may be added to the foam so that after use it will degrade over time in a landfill environment when disposed.

While open-cell polyurethane is one preferred material for the open-cell foam discussed herein, what is contemplated herein includes any open-cell foam (with at least some of the cells open), and produced from one or more polymers, such polymers including but not limited to EMA, ethylene vinyl acetate (EVA), ethylene-ethyl acrylate (EEA), ethylene-butyl acrylate (EBA), ethylene propylene diene monomer (EPDM), elastomers, polyolefin elastomers, low density polyethylene (LDPE), linear low density polyethylene (LLDPE), high density polyethylene (HDPE), polypropylene (PP), neoprene, styrene butadiene rubber, ionic co-polymers, other synthetic rubbers, natural rubber, chlorinated polyethylene (CPE), olefin block copolymers, ethylene maleic anhydride copolymer, very low density polyethylene (VLDPE), singe site initiated polyolefins, metallocene catalyzed polyolefins, silane-modified polymers (including but not limited to silane grafted, silane functionalized, and silane cross-linked polymers), maleic anhydride grafted polymers, styrene-butadiene-styrene copolymers, polyisoprene, and equivalents to any and all of these polymers. Silane modification of polymers can occur during the manufacturing process of the open-cell foam, or as a separate step after the foaming process, e.g., the silane can be applied in liquid form post-foaming. Further, specific silane-modified polymers may be tailored to target specific contaminants that may be present in water with bacteria, such as VOCs and SVOCs related to oils and/or industrial chemicals, metals (e.g. copper, iron, etc.) or metalloids (e.g. phosphorus) and other petroleum products, and surfactants, including but not limited to methylene blue active substances (MBAS).

The structure that includes or is made of open-cell foam can be fabricated into a number of different forms to suit the particular use scenario or application. One structure is an assembly of strips, typically 0.5-0.75 inch×0.5-0.75 inch×12-18 inches. The strips are fastened together tightly at the center to form a structure with multiple "fingers" or "blades." This structure exposes a large surface area to the environment and allows flow through (between the fingers of) the indicator. In some examples, these structures are then fastened to a rope line or similar tether with a weight at one end, and are submerged into the water body, leaving foam structures at various depths. Another alternative is to have strips of the foam that are anchored to the bottom and extend to the surface, over the entire water column; this is called "eelgrass" since it looks like eelgrass that grows in the ocean. Other forms can include strips and smaller cubes and pieces in other shapes. Another form includes a design that is shaped like a "water bug" and is cast into the water or water column with a fishing rod. Any form can be placed anywhere in the water column. Smaller pieces can be held in place in nets or other containers, such as plexiglass. Other forms include placing the open-cell foam into a jar and effectively "swabbing" the water that is placed or run from a tap into the jar. Additional forms include placing the open-cell foam structure into the air or at an air vent, waste water discharge location, a cooling tower, bathtub, shower, shellfish bed, river, lake, stream, and body of water, etc. and exposing to water or air for a period of time. The time period is non-limiting and can be from a few seconds or minutes to hours or days or more.

The monitoring/removal structure that comprises open-cell foam can also be made into a bracelet for humans to wear, in order to monitor a person's exposure over time to biological contaminants.

The structure that includes or is made of open-cell foam can be designed to monitor the water or air or surfaces for biological contaminants. The structure that includes or is made of open-cell foam can also be used to remove the contaminants from the water or air or surfaces. The structures can be in the forms of eelgrass, cubes, small pieces, and/or strips, and can be but need not be contained in a cylinder or net. These forms can be floating on the surface or suspended and/or submerged in the water column using anchors.

The structure that includes or is made of open-cell foam can be wiped or pushed over a surface to be remediated from pathogens, a process that is sometimes called "swabbing." Swabbing can pick up pathogens and biological contaminants that are on the surfaces that are swabbed. Swabbing can also pick up related contaminants. The foam material can be impregnated with a chemical-based or hydronium-based disinfectant/biocide before or after it is exposed to pathogens.

The exposure time can be minutes, hours, days, weeks, or months, depending on the situation and desired results. The biological and related contaminants, pathogens and viruses are detected and removed and killed by the impregnated open-cell foam structure. The open-cell foam can be impregnated or infused with the disinfectant/biocide before or after exposure to water, air, and/or surfaces. When used as an indicator, the un-impregnated structure can then be removed and tested for the presence (and potentially the concentration) of contaminants. The structure that includes or is made from open-cell foam, including but not limited to fabricated in the form of eelgrass, can be used to absorb and concentrate pathogens, thereby removing pathogens from water into the open-cell foam capillary network.

In some examples (e.g., in shellfish beds where the shellfish cannot be exposed to the disinfectant), the structure that includes or is made from open-cell foam is located in the bed, where it picks up pathogens. It is then removed from the water, and the disinfectant is then infused or applied to the open-cell foam after the open-cell foam is removed from the water, to kill the pathogens. If desired, the water, disinfectant and killed pathogens can be removed from the foam by wringing or otherwise squeezing the foam. The foam can then be re-used to pick up and remove more pathogens. This process of exposure, then disinfectant application, then squeezing, and re-use can be applied to water or air or surfaces.

In some examples biochar is used together with the foam. Biochar is an excellent adsorbent of organic matter, including pathogens. Biochar can be incorporated directly into the foam and/or it can be incorporated in a porous structure (like a sock) that is coupled to or carried by the structure that includes or is made up of the foam. Biochars and its used together with open-cell foam are further described in U.S. Patent Application Publication 2020/0156960, the entire disclosure of which is incorporated herein by reference.

Since the structure that includes or is made from open-cell foam can span different depths (or heights in the air), the results can determine the presence (and concentration) of one or more biological contaminants at different depths of the water (or air) or water column, from the surface to the bottom, or from the ground to a desired height, for example, and as desired.

Advantages of this biological remediator/indicator are its efficient cost, ease of deployment, durability during deployment and in use, and ability to collect samples for analysis over large volumes of water over an extended time period.

Upon retrieval of the indicator, the open-cell foam can be placed into a sealed container and sent to a qualified lab to test the open-cell foam matrix with various testing methods. More detail is provided elsewhere in this document.

Another significant attribute of the open-cell foam in one embodiment is utilizing a non-polar polymer with the result that the foam has no ionic charge. During the recent pandemic of 2020, the fact that paper towels, cotton rags, and cellulose sponges deactivate disinfectant because of their negative ionic charges came to the forefront as live pathogens including a virus like SARS-CoV-2 was left on surfaces thereby transmitting COVID-19 and infecting humans which include front line health care workers who were wearing full PPE gear and N95 masks. Paper towels, cotton rags, and cellulose sponges all have a negative ionic charge where the majority of disinfectants used (e.g. quats) have a positive ionic charge thereby cancelling each other out and rendering the disinfectant inactive leaving live pathogens on surfaces.

Deactivation of disinfectant is sometimes referred to as “quat binding.” The phenomenon of quat binding occurs when the active ingredient (quaternary ammonium chloride) becomes attracted to and absorbed into fabrics. The science behind how this happens is simple: Quats are positively charged ions and cotton and other natural textiles are negatively charged; positive attracts negative.

In United States Patent Publication US 2007/0142261 A1 entitled, “WIPER FOR USE WITH DISINFECTANTS” (incorporated by reference herein), the problems with quat binding and deactivation of disinfectant are well established.

What makes the subject open-cell foam invention unique is the high surface area for absorption and release of active disinfectant that substantially mitigates the risk of gaps in surface coverage or not making contact with live pathogens on surfaces. The high surface area combined with a neutral ionic charge, assures no deactivation of disinfectant/biocide along with maximum delivery of disinfectant/biocide per square inch of surface area.

Furthermore, based on validation testing, these results have proven the ability of the open-cell foam biological indicator to detect *Legionella* at low levels where conventional grab samples can show non-detects when in fact *Legionella* was present. Data is set forth elsewhere.

In one aspect a method of killing pathogens includes providing a structure that comprises an open-cell polymer foam, impregnating the open-cell foam with a substance that comprises a biocide or another chemical that can kill pathogens, and exposing the structure to the pathogens such that the impregnated open-cell foam contacts and kills the pathogens.

In an example the pathogens are on a surface or in air or in water. In an example exposing the structure to the pathogens comprises moving the structure over the surface such that the impregnated open-cell foam contacts the pathogens, removes the pathogens from the surface, and kills the pathogens.

In another aspect a method of remediating pathogens that are on a surface includes providing a structure that comprises an open-cell polymer foam, applying a disinfectant that can kill pathogens to one or both of the surface and the open-cell polymer foam, and moving the structure over the surface such that the open-cell foam contacts the pathogens, removes the pathogens from the surface, and the pathogens are killed. In an example the disinfectant comprises at least one of a chemical-based disinfectant and a hydronium-based disinfectant.

In another aspect a method of remediating pathogens includes providing a structure that comprises an open-cell polymer foam, exposing the structure to at least one of air and water such that the open-cell foam contacts pathogens, and either before or after the exposing step, applying to the open-cell polymer foam a disinfectant that can kill pathogens, to kill pathogens that come into contact with the foam.

In an example the disinfectant comprises at least one of a chemical-based disinfectant and a hydronium-based disinfectant. In an example the structure comprises a face mask that is configured to be worn by a person covering at least one of the mouth and nostrils. In an example the structure is located at least in part in a building ventilation system. In an example the disinfectant is applied after the exposing step. In some examples the method further includes wringing out the foam after the application of the disinfectant, to remove at least some of the disinfectant from the foam. In an example the method further includes reusing the wrung-out foam by exposing it a second time to at least one of air and water such that the open-cell foam contacts pathogens.

In an example the application of disinfectant comprises impregnating the foam with the disinfectant. In some examples the method further includes incorporating biochar into the open-cell foam or coupling biochar to the structure. In an example the biochar is held in a porous container that is coupled to the structure.

BRIEF DESCRIPTION OF THE DRAWING

The drawing depicts one non-limiting example of the placement of open-cell foam material into a body of water, as a step in the collection and removal from the water and neutralization or killing of biological and microbiological contaminants and pathogens.

DETAILED DESCRIPTION OF EXAMPLES

Methods of removing biological contaminants and pathogens from a body of water or the air or surfaces are disclosed. The methods also generally involve killing the pathogens using a disinfectant/biocide that is carried by the open-cell foam structure. Since the open-cell foam has a very large surface are, more disinfectant can be carried as compared to other wipes. Also, the oleophilic/hydrophobic nature of the open-cell foam is effective to absorb/adsorb large amounts of pathogens, leading to better remediation results as compared to the use of paper towels or other wipes or wipers.

As a first step, an open-cell foam material (or other foam materials, as described elsewhere herein) can be placed into water or into the air, or water or air can be passed though the material. The placement can be at one or more locations in the body of water or air, and at one or more depths or heights in the body of water or in the air. After desired exposure times, one or more separate portions of the open-cell foam material are removed from the water or air. The foam can be impregnated with a disinfectant/biocide either before or after it picks up the pathogens from the air, water and/or surfaces it is moved over. In some examples the presence in the removed separate portions of one or more biological contaminants that were removed from the water or air by the open-cell foam material are then determined, typically by standard testing procedures well known in the art for the particular type of biological contaminant(s).

In an example the foam structure is placed in a building ventilation system such that ventialation air passes through the foam. The foam captures pathogens in the air. The foam can be treated with the liquid disinfectant either before or after it is exposed to the air, to kill the pathogens. The previously-exposed foam can be wrung out or squeezed to remove liquid disinfectant, and then reused for additional exposures and pathogen remediation using additional disinfectant. In another example the foam can be configured as a face mask that is worn by a person covering one or both of the mouth and nostrils. The foam absorbs pathogens such as virus particles. The pathogens can then if desired be killed by applying the disinfectant to the foam, or the foam can be safely disposed of without the use of disinfectant. If foam is to be re-used, used disinfectant can be removed, e.g., by wringing out or squeezing the foam to remove liquid disinfectant. The foam can then be used all over again.

There are several different preferred water testing methods with the open-cell foam. Non-limiting examples include the following. In a first example, a grab sample can be taken by placing a piece of the open-cell foam in a sample jar and then partially or fully filling the jar with water. The foam can be removed for testing after any desired exposure time. If necessary to help preserve specimens that are collected by the foam, the container with water and foam can be placed on ice until the foam is ready to be tested; however, ice is not necessarily required. In a second example, the open-cell foam can be placed directly into a stream or body of water to be tested. Exposure times can vary; non-limiting examples are 5, 10, or 20 minutes. The foam is then removed from the water and tested. In a third example, cumulative testing can be accomplished by placing the foam into water to be tested, and then periodically removing portions of the foam at different exposure times.

The methods are effective both to determine the presence of and kill pathogens and biological contaminants in the water or air or on surfaces, and also to remove such contaminants from the water or air or surfaces. The methods thus can be used for contaminant detection and/or filtration or remediation.

The drawing depicts three groups of strips or "blades" of open-cell foam material 12, 14 and 16. Each group has multiple strips that are held together at about their centers. The groups are fastened to a line 32 that is held on the bottom 24 of water body 20 by weight or anchor 30. In this example group 16 floats on the water surface 22, while groups 12 and 14 are held at different depths below the surface. This disclosure allows for the placement of open-cell foam material at any one or more heights of a body of water and/or the air, and at one or more locations in the body of water or air. Various non-limiting methods of exposing the open-cell material to water or air are described herein; any such method can be used as desired or as necessary depending on the body of water or the air mass, and/or the testing regime that is desired under the circumstances.

After desired exposure times, one or more portions of the foam material are removed from the water or air. This can be done by clipping or cutting a piece of foam, or removing an entire group or other portion or separate piece of foam, for example. The exposure times can be from seconds to minutes to hours to days to weeks to months, depending on the particular testing regime. Since the open-cell foam absorbs and adsorbs biological contaminants, the removed portions of the foam can be tested for particular biological contaminant(s) that are expected or are being investigated. The foam can act as an accumulator for these biological contaminants. Also, the different locations and different exposure times allow for a tailored review of biological contaminants, their locations, and their movement within the water or air.

The subject materials have been used in testing of potable water. Test methods and results follow.

Results of uses of the biological indicator in water are disclosed in the appendices 1-5 of the priority Provisional application, which are incorporated by reference herein in their entireties. A brief discussion of those appendices follows.

Appendix 1 that was part of the Provisional Application that is incorporated herein by reference (four pages) is a report from an independent testing laboratory that details the study design, procedures, and results, for comparison of grab samples (prior art) to testing using the open-cell foam of the present disclosure in potable water. The results prove that the open-cell foam acts as a biological indicator, as it is effective to remove and detect *Legionella* at low levels, where conventional grab samples can show non-detects when in fact *Legionella* is present.

Appendix 1 included the following:

A purpose of this study was to identify an effective method for the extraction of *Legionella* from an open-cell foam environmental indicator sampling device. Replicate sponge devices (i.e., pieces of the open-cell foam) were indirectly inoculated with a mixed suspension of fresh *Legionella* cultures at three target concentrations: low (1-10 CFU/mL), medium (10-100 CFU/mL) and high (100-1,000 CFU/mL). The recovery and detection procedure of the pathogen was evaluated using a non-ionic surfactant (Polysorbate 80) in conjunction with a maceration extraction process and nutritive media (BCYE agars) culturing following a modification of the Centers for Disease Control and Prevention (CDC) "Procedures for the Recovery of *Legionella* from the Environment", January 2005. A summary of the study design is presented in Table A below.

TABLE A

*Legionella* Recovery Study Design Summary

| Mixed *Legionella* suspension | Matrix | Target Level | Target Concentration | Maceration Extraction Procedure | Surfactant |
|---|---|---|---|---|---|
| *Legionella pneumophila* ATCC[1] 33152 | Sterile Tap Water | Low | 1-10 CFU/mL | Blending | Polysorbate 80[3] |
| *Legionella dumoffii* QL14012[2]-1A | | Medium | 10-100 CFU/mL | | |
| | | High | 100-1,000 CFU/mL | | |

TABLE A-continued

| Legionella Recovery Study Design Summary | | | | | |
|---|---|---|---|---|---|
| Mixed *Legionella* suspension | Matrix | Target Level | Target Concentration | Maceration Extraction Procedure | Surfactant |
| *Legionella micdadei* QL145022-1A | | | | | |

[1]ATCC: American Type Culture Collection
[2]QL: Q Laboratories, Inc. Culture Collection
[3]The polysorbate was Tween™ 80, which is a registered trademark of Croda Americas, Inc.

The study included three replicate open-cell sponge samples indirectly inoculated for each target contamination level with *Legionella* species. For each contamination level, one liter of sterile tap water was inoculated using a mixed suspension of the *Legionella* cultures that had been diluted to the targeted levels. To simulate real-world environmental sampling, each open-cell device was submerged and allowed to absorb the contaminated water for 3-5 minutes. During submersion, the sponges were mixed in a bobbing motion using sterile pipettes. The sponges were then placed into the original sample glass vial and approximately 200 mL of the contaminated water added and the lid tightly capped. Samples remained at ambient temperature (20-24° C.) for approximately 24 hours prior to analysis.

*Legionella* Extraction and Detection

Extraction

All metals rings and zip ties were aseptically removed from each sponge sample prior to transferring all sample contents to a sterile laboratory blender jar. A one milliliter volume of a sterile, non-ionic surfactant, Tween™ 80, was added to each blender jar to facilitate the release of any *Legionella* organisms that may be present within the pores of the sampling device.

Open-cell sponge samples were blended for two minutes and the jars allowed to rest for approximately ten minutes, which provided sufficient time for the sponge particulate matter to float to the surface. The liquid portion of each blender jar was aseptically transferred to sterile conical tubes and centrifuged at 5500×g for thirty minutes at ambient temperature (20-24° C.). All but five milliliters of the supernatant was aseptically removed and discarded into approved biohazard containers.

Detection

The remaining five milliliters of sample was homogenized by vortex and an aliquot spread plated onto BCYE, PCV, GPCV and PCV (−) microbiological agar plates and incubated aerobically at 35±1° C. to encourage the proliferation of *Legionella* organisms. The presence or absence of typical *Legionella* colonies based on morphology and/or fluorescence was determined after 72 to 96 hours of incubation. If any agar plates did not appear to contain typical colonies, incubation was extended for an additional seven days.

Typical colonies from each contamination level replicate were re-struck to selective and non-selective media. Typical colonies were then confirmed via serological latex agglutination and molecular identification using the Bruker MS Biotyper.

The results obtained from this method development study indicate that overall, the extraction procedure had positive outcomes for removing *Legionella* microorganisms the open-cell foam environmental sampling device. The novel open-cell foam sponges evaluated in this study were inoculated at levels as low as about 4 (e.g. 3.5) CFU/mL, or as high as approximately 250 CFU/mL. Inoculation of the device paralleled actual sampling procedures employed in the field. Whether the pathogen is present at a level of a few cells or many thousands of cells per milliliter, the ability to capture, extract, and detect the organism reliably and consistently is paramount to maintaining the good health of the building occupants. The detection of *Legionella* is dependent upon the sampling device or procedure used in addition to the laboratory method employed. One cannot be successful without the other.

The cultural detection and confirmation of *Legionella* at all levels for all replicates demonstrates the method has applicability as a viable option for *Legionella* analysis in routine water samples. See Tables B and C for detailed inoculum and recovery results.

TABLE B

| Inoculum Results | | | | | |
|---|---|---|---|---|---|
| Mixed *Legionella* suspension | Matrix | Target Level | Mixed Inoculum Concentration | Extraction Procedure | Surfactant |
| *Legionella pneumophila* ATCC 33152 | Sterile Tap Water | Low | 3.5 CFU/mL | Blending | Polysorbate 80 |
| *Legionella dumoffii* QL14012-1A | | Medium | 20.6 CFU/mL | | |
| | | High | 247.5 CFU/mL | | |
| *Legionella micdadei* QL145022-1A | | | | | |

TABLE C

Detailed Recovery Results

| Examination for Typical *Legionella* | | | | | | | Confirmation | | | | | | | |
|---|---|---|---|---|---|---|---|---|---|---|---|---|---|---|
| | | | | | | | | | | Slide Agglutination | | | | Bruker |
| Contamination | | PCV | | GPCV | | PCV | | PCV | | Test | | | | Biotyper |
| Level/Replicate | BCYE | A | B | A | B | (−) | BCYE[a] | (−) | SBA | 1 | 2-15 | L. spp. | Result | ID |
| Low A | + | + | − | + | + | − | + + | − | − | + + | − | − | Positive | *Legionella pneumophila* |
| Low B | + | + | + | − | + | − | + + | − | − | + | − | + | Positive | *Legionella pneumophila*, *Legionella dumoffii* |
| Low C | + | + | + | + | + | − | + + | − | − | + + | − | − | Positive | *Legionella pneumophila* |
| Medium A | + | + | + | + | + | − | + + | − | − | + | − | + | Positive | *Legionella pneumophila*, *Legionella dumoffii* |
| Medium B | + | + | + | + | + | − | + + | − | − | + | − | + | Positive | *Legionella pneumophila*, *Legionella micdadei* |
| Medium C | + | + | + | + | + | − | + + | − | − | + + | − | − | Positive | *Legionella pneumophila* |
| High A | + | + | + | + | + | − | + + | − | − | + + | − | − | Positive | *Legionella pneumophila* |
| High B | + | + | + | + | + | − | + + | − | − | + + | − | − | Positive | *Legionella pneumophila* |
| High C | + | + | + | + | + | − | + + | − | − | + | − | + | Positive | *Legionella pneumophila*, *Legionella micdadei* |
| Sterility Control | − | − | − | − | − | − | − | − | − | NA | NA | NA | Typical | NA |
| Negative Control | − | − | − | − | − | − | − | − | − | − | − | − | Typical | NA |
| Positive Control | + | + | + | + | + | − | + | − | − | + | − | + | Typical | *Legionella pneumophila* |

[a]Two typical *Legionella* colonies picked for serological confirmation and molecular identification The procedure to extract *Legionella* from the open-cell foam environmental sampling device was adapted based on previous works for detecting *Legionella* from environmental samples. The positive outcomes of this study following the procedures presented above, as well as experience working with similar sampling devices, has prompted possibilities of streamlining the method to better suit the workflow in a routine laboratory environment. Blending the device requires sterile laboratory blender jars with sharp blades and potentially poses a safety risk if not performed in a careful manner and in a Biological Safety Cabinet (BSC). One alternative to blending is to place the sampling device into a common sterile laboratory blender bag with Tween™ 80 and extract the bacteria by homogenizing with a laboratory paddle blender. This procedure would not only decrease the time required for processing the sample but also allow for the use of readily available disposable sterile materials used by a majority of testing laboratories. Selecting blender bags would have the additional benefit of increasing the ease of use factor, thereby improving laboratory technician efficiency.

The inoculation method utilized in this laboratory study followed the prescribed, real world best practices for correctly sampling with the sponge device: the glass jars containing the sponges were filled with the sample water to be tested.

Appendices 2-5 that were part of the Provisional Application that is incorporated herein by reference (two pages each) included reports from independent lab testing from Flint MI—where bacteria has been a continued challenge with the water distribution system and potential reported human health effects. For the testing with the open-cell foam biological indicator the lab used the following tests and methods:

| TEST | METHOD |
|---|---|
| Aerobic Plate Count (APC) | FDA Bacteriological Analytical Manual |
| Coliform | AOAC 991.14 |
| *Legionella* | Centers for Disease Control (January 2005) |
| Microbial Identification | Bruker MALDI Biotyper (Q Labs SOP #10-MIDL-METH-001A) |

For the testing for the water grab samples the lab used the following test and method:

| TEST | METHOD |
|---|---|
| Aerobic Plate Count (APC) | Standard Methods for the Examination of Water and Wastewater, $22^{nd}$ Edition |

Appendix 2 shows lower to <10 or <1 (non-detect) APC counts on grab samples while the open-cell foam biological indicator ("Waterbug") shows APCs in the millions and identifies bacteria of concern. The following is from appendix 2.

The following results were obtained from the samples submitted for assay:

Methodology

| TEST | METHOD |
|---|---|
| Aerobic Plate Count (APC) | Standard Methods for the Examination of Water and Wastewater, 22nd Edition |

Results

| Sample No. | IDENTIFICATION OF SAMPLE | APC/mL |
|---|---|---|
| 1 | 1608640-01A (Upstairs Bath Grab for Bacteria/Fungi) | 4,400 |
| 2 | 1608640-05A (Water Meter Grab for Bacteria/Fungi) | <10 |

Methodology

| TEST | METHOD |
|---|---|
| Aerobic Plate Count (APC) Analytical Manual Identification | FDA Bacteriological Gram Stain & VITEK |

Results

| Sample No. | IDENTIFICATION OF SAMPLE | APC/sponge | Identification |
|---|---|---|---|
| 1 | 1608640-03B (Upstairs Bath WaterBug Grab) | 3,800,000 | *Acinetobacter junii*, *Brevibacillus* |
| 2 | 1608640-07B (Water Meter WaterBug Grab) | 2,900,000 | *Pseudomonas aeruginosa*/ *Pseudomonas putida*, |

Appendix 3 shows no APC count on the grab sample while the open-cell foam biological indicator ("Waterbug") shows an APC count of >570,000 and identifies bacteria of concern *Pseudomonas aeruginosa.*

The following results were obtained from the samples submitted for assay:

Methodology

| TEST | METHOD |
|---|---|
| Aerobic Plate Count (APC) | Standard Method for the Examination of Water and Wastewater, 22nd Edition |

Results

| Sample No. | IDENTIFICATION OF SAMPLE | APC/mL |
|---|---|---|
| 1 | 1609132-04A (Amber Grab for Bacteria/Fungi) | <1 |

Methodology

| TEST | METHOD |
|---|---|
| Aerobic Plate Count (APC) Identification | FDA Bacteriological Analytical Manual Gram Stain & VITEK |

Results

| Sample No. | IDENTIFICATION OF SAMPLE | APC/sponge | Identification |
|---|---|---|---|
| 1 | 1609132-03B (WaterBug Grab 5 mins) | >570,000 | *Pseudomonas aeruginosa* |

Appendix 4 shows lower to <1 (non-detect) APC counts on grab samples while the open-cell foam biological indicator ("Waterbug") shows APCs>570,000 and identifies bacteria.

The following results were obtained from the samples submitted for assay:

Methodology

| TEST | METHOD |
|---|---|
| Aerobic Plate Count (APC) Identification | FDA Bacteriological Analytical Manual Gram Stain & VITEK |

Results

| Sample No. | IDENTIFICATION OF SAMPLE | APC/mL | Identification |
|---|---|---|---|
| 1 | 1609134-01A (Water Meter Amber Grab for Bacteria/Fungi) | <1 | N/A |
| 2 | 1609134-05A (Shower Amber Grab for Bacteria/Fungi) | 3,100 | *Bacillus simplex* |

Methodology

| TEST | METHOD |
|---|---|
| Aerobic Plate Count (APC) Analytical Manual Identification | FDA Bacteriological Gram Stain & VITEK |

Results

| Sample No. | IDENTIFICATION OF SAMPLE | APC/sponge | Identification |
|---|---|---|---|
| 1 | 1609134-03B (Water Meter Grab WaterBug) | >570,000 | *Pseudomonas fluorescens* |
| 2 | 1609134-07B (Shower Grab WaterBug) | >570,000 | *Acinetobacter* species |

Appendix 5 shows low APC counts (11,000 and <1) while the open-cell foam biological indicator ("Waterbug") shows APC counts of 150,000 and >570,000.

The following results were obtained from the samples submitted for assay:

Methodology

| TEST | METHOD |
| --- | --- |
| Aerobic Plate Count (APC) | FDA Bacteriological Analytical Manual |
| Identification | Gram Stain & VITEK |

Results

| Sample No. | IDENTIFICATION OF SAMPLE | APC/sponge | Identification |
| --- | --- | --- | --- |
| 1 | 1609133-03B (Murphy Water Meter WaterBug Grab) | 150,000 | Delftia acidovorans |
| 2 | 1609133-07B (Murphy Shower Grab WaterBug) | >570,000 | Brevundimonas diminuta/vesicularis |

Methodology

| TEST | METHOD |
| --- | --- |
| Aerobic Plate Count (APC) | FDA Bacteriological Analytical Manual |
| Identification | Gram Stain & VITEK |

Results

| Sample No. | IDENTIFICATION OF SAMPLE | APC/mL | Identification |
| --- | --- | --- | --- |
| 1 | 1609133-01A (Murphy Water Meter Amber Grab for Bacteria/Fungi) | 11,000 | *Rhodotorula* sp. |
| 2 | 1609133-05A (Murphy Shower Amber Grab for Bacteria/Fungi) | <1 | N/A |

A second report from an independent testing laboratory details the study design, procedures, and results, for the evaluation of the ability for six different types of the subject open-cell foam sampling devices (i.e., WaterBugs) in recovering and releasing select bacteria from a water source. In this study, a bulk lot of sterile tap water was inoculated with *Pseudomonas aeruginosa*. Traditional "grab samples" consisting of three (3) replicate 100 mL volumes were collected to establish starting baseline bacterial counts for evaluation purposes. WaterBug sampling devices, comprised of six different design formulations, and in replicates of three, were submerged for a total of 20 minutes. During submersion the inoculated water was periodically mixed to maintain homogeneity and even distribution of the bacteria. After 20 minutes had elapsed, each WaterBug was transferred individually to a sterile stomacher bag. Customary laboratory procedures for extracting bacteria from matrices involve the use of a laboratory paddle blender, or "stomacher". One point of focus for this study was to determine the stomaching time for optimal recovery; therefore an aliquot from each bag was removed after being stomached for 30 seconds, 1 minute, and 2 minutes. At each time point, the aliquot was diluted as appropriate and the concentration of target organism determined using standard microbiological plate count techniques. Final bacterial counts of the inoculated water were determined after the WaterBugs were removed by obtaining three 100 mL traditional grab samples and enumerating as previously described. A summary of the WaterBug formulations tested and study summary is presented in Table A below.

TABLE A

*Pseudomonas* Retention and Release Study Design Summary

| WaterBug Formulation | Matrix | Target Organism | Extraction Procedure | Plating Medium/ Incubation |
| --- | --- | --- | --- | --- |
| A: Open-cell EMA<br>B: Closed-cell EMA<br>C1: Open-cell LDPE/8452<br>C2: Open-cell EVA/8452 Large-cell<br>C3: Open-cell EVA/8452 Small-cell<br>D: Open-cell urethane | Sterile Tap Water | *Pseudomonas aeruginosa* ATCC 15442 | Stomaching (30 s, 1 min, 2 min) | MacConkey agar 35° C. for 24 ± 2 hours |

*Pseudomonas aeruginosa* Extraction and Enumeration

Extraction

Prior to submersing the WaterBugs, 3×100 mL grab samples were taken from the inoculated sterile tap water. The WaterBugs were removed after 20 minutes of submersion in the inoculated sterile tap water and were stomached for 30 seconds, 1 minute, and 2 minutes. An aliquot of sterile tap water was removed at each time point. An additional 3×100 mL grab samples were taken from the inoculated sterile tap water once the WaterBugs had been removed.

Enumeration

The grab samples and the aliquots of the inoculated sterile tap water removed at the three pre-determined time points for each of the WaterBug formulations was plated onto MacConkey agar in duplicate. The dilutions were spread plated and incubated at 35±1° C. for 24±2 hours. Typical colonies were enumerated and recorded as CFU/plate, then averaged and multiplied by the dilution factor to determine the amount of microorganisms present in the inoculated sterile tap water sample at the beginning and end of testing as well as the concentration recovered from each of the different sponge design formulations.

The average CFU/mL, expressed as normalized values ($Log_{10}$), recovered from each WaterBug design formulation was compared to the average initial grab samples prior to submersion to obtain percent recovery at each time point in the bacterial extraction process (30 sec., 1 min., 2 min.). Of the six WaterBug formulations tested, Type A: Open-cell EMA demonstrated the highest retention and subsequent release of the inoculating organism at 88.8% after a 1 minute stomaching time period. Type B: Closed-cell EMA demonstrated the lowest retention and release after 2 minutes of stomaching at 70.5%. Type C2: Open-cell EVA/8452 Large-cell was the only formulation to show an increase in percent recovery at the final stomaching time point. This may suggest that it performed best at retaining liquid and bacteria compared to the other formulations; however, the concentration of trapped bacteria that were released was less than other designs on average. Comparing the difference of means between the initial grab sample counts and mean $Log_{10}$ counts for each sampling time point demonstrates significant differences (>0.5 $Log_{10}$) with several of the design formulations. Tables B and C present the results of the percent recovery and the difference of means.

TABLE B

| Grab Sample Recovery Results | | |
|---|---|---|
| Grab Samples | Average CFU/mL | $Log_{10}$ CFU/mL |
| Initial | $3.9 \times 10^2$ | 2.5911 |
| Final | $3.3 \times 10^1$ | 1.5185 |

TABLE C

Sponge Formulation Statistical Data

| | 30 sec. Stomach | | | | 1 min. Stomach | | |
|---|---|---|---|---|---|---|---|
| Sponge Formulation | CFU/mL | $Log_{10}$ CFU/mL | % Recovery[1] | Mean Difference[2] | CFU/mL | $Log_{10}$ CFU/mL | % Recovery[1] |
| A: Open-cell EMA | $2.0 \times 10^2$ | 2.3010 | 88.8 | 0.2901 | $2.0 \times 10^2$ | 2.3010 | 88.8 |
| B: Closed-cell EMA | $9.7 \times 10^1$ | 1.9868 | 76.7 | 0.6043 | $1.0 \times 10^2$ | 2.0000 | 77.2 |
| C1: Open-cell LDPE/8452 | $1.3 \times 10^2$ | 2.1139 | 81.6 | 0.4772 | $1.2 \times 10^2$ | 2.0792 | 80.2 |
| C2: Open-cell EVA/8452 Large-cell | $1.4 \times 10^2$ | 2.1461 | 82.8 | 0.4450 | $1.3 \times 10^2$ | 2.1139 | 81.6 |
| C3: Open-cell EVA/8452 Small-cell | $1.0 \times 10^2$ | 2.0000 | 77.2 | 0.5911 | $1.1 \times 10^2$ | 2.0414 | 78.8 |
| D: Open-cell Urethane | $1.6 \times 10^2$ | 2.2041 | 85.1 | 0.3870 | $1.2 \times 10^2$ | 2.0792 | 80.2 |

| | 1 min. Stomach | 2 min. Stomach | | | |
|---|---|---|---|---|---|
| Sponge Formulation | Mean Difference[2] | CFU/mL | $Log_{10}$ CFU/mL | % Recovery[1] | Mean Difference[2] |
| A: Open-cell EMA | 0.2901 | $1.7 \times 10^2$ | 2.2304 | 86.1 | 0.3607 |
| B: Closed-cell EMA | 0.5911 | $6.7 \times 10^1$ | 1.8261 | 70.5 | 0.7650 |
| C1: Open-cell LDPE/8452 | 0.5119 | $1.3 \times 10^2$ | 2.1139 | 81.6 | 0.4772 |
| C2: Open-cell EVA/8452 Large-cell | 0.4772 | $1.6 \times 10^2$ | 2.2041 | 85.1 | 0.3870 |
| C3: Open-cell EVA/8452 Small-cell | 0.5497 | $1.0 \times 10^2$ | 2.0000 | 77.2 | 0.5911 |
| D: Open-cell Urethane | 0.5119 | $1.1 \times 10^2$ | 2.0414 | 78.8 | 0.5497 |

[1]% recovery calculated using the $Log_{10}$ CFU/mL mean average at each sampling time point and the initial grab sample $Log_{10}$ CFU/mL mean average
[2]A mean difference absolute value of greater than 0.5 indicates a statistical significant difference between counts In some examples a chemical-based and/or hydronium-based disinfectant is used with the open-cell foam structure. Chemical-based disinfectants include but are not limited to alcohols, hydrogen peroxide, quaternary ammonium chlorides (quats), and other pathogen disinfectants that are well known in the field and so not further described herein, including but not limited to those described in U.S. Pat. Nos. 6,331,514 and 8,940,792 and U.S. Patent Application Publication 2007/0142261. Hydronium-based disinfectants are well known in the field and so are not further described herein, including but are not limited to those described in U.S. Pat. Nos. 10,039,696 and 9,204,633. The disclosures of each of these patents and publications are incorporated by reference herein for all purposes.

In an example a number of strips of open-cell foam that were infused with hydronium-based Hy-IQ sanitizer available from Aphex Biocleanse Systems, Inc. of Pittsford, NY were placed into contaminated water from a body of water contaminated with fecal coliform from a water-treatment plant. All pathogens were killed.

The invention is not limited by the above description but rather is supported by it. Other options will occur to those skilled in the art and are within the scope of the following claims.

What is claimed is:

1. A method of killing pathogens, comprising:

providing a structure that comprises an open-cell polymer foam;

incorporating biochar into the open-cell polymer foam or coupling biochar to the structure;

impregnating the open-cell polymer foam of the structure with a hydronium-based disinfectant that is configured to kill pathogens; and exposing the disinfectant-impregnated open-cell polymer foam of the structure to the pathogens such that the disinfectant-impregnated open-cell polymer foam of the structure contacts and kills the pathogens.

2. The method of claim 1, wherein the pathogens are on a surface or in air or in water.

3. The method of claim 2, wherein exposing the disinfectant-impregnated open-cell polymer foam of the structure to the pathogens comprises moving the disinfectant-impregnated open-cell polymer foam of the structure over the surface such that the disinfectant-impregnated open-cell polymer foam of the structure contacts the pathogens, removes the pathogens from the surface, and kills the pathogens.

4. A method of remediating pathogens, comprising:
- providing a structure that comprises an open-cell polymer foam;
- incorporating biochar into the open-cell polymer foam or coupling biochar to the structure;
- exposing the structure to at least one of air and water such that the open-cell polymer foam of the structure contacts pathogens; and
- either before or after the exposing step, applying to the open-cell polymer foam of the structure a hydronium-based disinfectant that is configured to kill pathogens that come into contact with the open-cell polymer foam of the structure.

5. The method of claim 4, wherein the structure comprises a face mask that is configured to be worn by a person covering at least one of the mouth and nostrils.

6. The method of claim 4, wherein the structure is located at least in part in a building ventilation system.

7. The method of claim 4, wherein the hydronium-based disinfectant is applied after the exposing step.

8. The method of claim 7, further comprising wringing out the open-cell polymer foam after the application of the hydronium-based disinfectant, to remove at least some of the hydronium-based disinfectant from the open-cell polymer foam.

9. The method of claim 8, further comprising reusing the wrung-out open-cell polymer foam by exposing the structure a second time to at least one of air and water such that the open-cell polymer foam of the structure contacts pathogens.

10. The method of claim 4, wherein the applying to the open-cell polymer foam a hydronium-based disinfectant comprises impregnating the open-cell polymer foam with the hydronium-based disinfectant.

11. The method of claim 4, wherein the biochar is held in a porous container that is coupled to the structure.

12. A method of remediating pathogens, comprising:
- providing a structure that comprises an open-cell polymer foam;
- incorporating biochar into the open-cell polymer foam or coupling biochar to the structure;
- exposing the structure to at least one of air and water such that the open-cell polymer foam contacts pathogens; and
- either before or after the exposing step, applying to the open-cell polymer foam a disinfectant that is configured to kill pathogens that come into contact with the open-cell polymer foam.

* * * * *